(12) United States Patent
Shi et al.

(10) Patent No.: US 6,896,915 B2
(45) Date of Patent: May 24, 2005

(54) USE OF CONVERTED LOW-VISCOSITY, HIGH SOLIDS STARCH IN FOODS

(75) Inventors: Yong-Cheng Shi, Hillsborough, NJ (US); Chung-Wai Chiu, Westfield, NJ (US); David P. Huang, Bound Brook, NJ (US); Danuta Janik, North Brunswick, NJ (US)

(73) Assignee: National Starch and Chemical Investment Holding Corporation, New Castle, DE (US)

( * ) Notice: Subject to any disclaimer, the term of this patent is extended or adjusted under 35 U.S.C. 154(b) by 650 days.

(21) Appl. No.: 10/008,802

(22) Filed: Nov. 13, 2001

(65) Prior Publication Data

US 2003/0099744 A1 May 29, 2003

(51) Int. Cl.$^7$ ................................................ A23L 1/05
(52) U.S. Cl. ........................ 426/20; 426/103; 426/661; 426/658; 426/302; 127/65; 127/67; 127/71
(58) Field of Search .......................... 426/96, 103, 661, 426/658, 20, 302; 127/65, 67, 71

(56) References Cited

U.S. PATENT DOCUMENTS

| | | | | |
|---|---|---|---|---|
| 4,645,674 A | * | 2/1987 | Lang et al. ..................... | 426/94 |
| 4,762,721 A | * | 8/1988 | Holscher et al. .............. | 426/94 |
| 4,822,626 A | * | 4/1989 | Spanier et al. ................ | 426/94 |
| 4,977,252 A | | 12/1990 | Chiu ........................... | 536/102 |
| 5,185,176 A | * | 2/1993 | Chiu ........................... | 426/651 |
| 5,194,284 A | * | 3/1993 | Chiu et al. .................... | 426/589 |
| 5,225,222 A | * | 7/1993 | Cha et al. ..................... | 426/89 |
| 5,254,353 A | | 10/1993 | Huang et al. ................. | 426/94 |
| 5,569,483 A | | 10/1996 | Timonen et al. ............. | 426/658 |
| 5,599,569 A | | 2/1997 | Chiu et al. .................... | 426/48 |
| 5,756,140 A | * | 5/1998 | Shoop et al. ................ | 426/302 |
| 5,965,180 A | | 10/1999 | Lonergan ..................... | 426/94 |

FOREIGN PATENT DOCUMENTS

| | | | |
|---|---|---|---|
| EP | 0 242 913 | 10/1987 | .......... C12P/19/22 |
| EP | 0 480 433 A2 | 4/1992 | .......... A23L/1/325 |
| JP | 57144948 | 9/1982 | ............. A23L/1/00 |
| JP | 57166943 | 10/1982 | ............. A23L/1/00 |
| WO | WO 97/00620 | 1/1997 | ............ A23G/3/30 |

OTHER PUBLICATIONS

Red Arrow Products Company LLC, "Tru Gold™", 633 South 20$^{th}$ Street, Manitowoc, WI 54220–1537.

Par–Way Tryson Company, "Bake–Sheen", 107 Bolte Lane, St. Clair, Mo 63077.

Par–Way Tryson Companies, The Makers of "Vegelene", 107 Bolte Lane, St. Clair, Mo 63077.

* cited by examiner

*Primary Examiner*—N. Bhat
(74) *Attorney, Agent, or Firm*—David P. LeCroy

(57) ABSTRACT

The present invention relates to a method for glazing a food comprising applying a solution of a glaze base containing a converted starch to the food and drying the food; a process for preparing the starch; the starch prepared therefrom; and a glaze comprising the glaze bases thereof.

22 Claims, No Drawings

US 6,896,915 B2

USE OF CONVERTED LOW-VISCOSITY, HIGH SOLIDS STARCH IN FOODS

FIELD OF THE INVENTION

The present invention relates to a method for glazing a food comprising applying a solution of a glaze base containing a converted starch to the food and drying the food; a process for preparing the starch; the starch prepared therefrom; and a glaze comprising the glaze bases thereof.

BACKGROUND OF THE INVENTION

In the commercial production of cereals, snacks and bakery products, glazes have customarily been applied as coatings to the surfaces of the food products to enhance their flavor and customer appeal. Glazes have typically been used to seal the surface of the food product and to provide a high sheen to the product. Additionally, where the food product is not completely coated with an icing the glaze serves as a barrier between the relatively high-moisture food product and the relatively low-moisture icing.

Currently, most effective glazes are protein-based, being composed of eggs or compositions containing protein additives designed to replicate the action of egg components. Glazes composed of eggs must be used before cooking as the cooking process imparts the characteristic transparent films on the surface of the food products. Moreover, the liquid egg-coating material must be carefully maintained below 40° F. to maintain its structure and reduce the development of off-flavors and microbial growth and is widely recognized as a potential source of quality control problems.

While not being susceptible to the same quality control problems, egg-free glazes developed for use after baking have not been totally satisfactory in sealing the surface of the food product. In particular, starch-based products are often undesirably sticky, exhibit unacceptably high viscosity, and cannot be prepared at solids contents of greater than 30%. Moreover, the viscosity of these product is not stable and increases unacceptably over time. Presently commercially available glazes containing starch require additional components designed to alleviate these deficiencies.

There is a need in the food industry for a stable, low viscosity, high sheen glaze which provides a good surface seal on food products.

SUMMARY OF THE INVENTION

It has been discovered that starch provides a stable, low viscosity, glaze which provides a high sheen and good surface seal on food products.

The present invention is directed to a method for glazing a food comprising the steps of:
a) applying an aqueous solution containing from about 25% to about 65% by weight of a glaze base containing a converted starch to the food; and
b) drying the food;
wherein the glaze base has a funnel viscosity, measured at 19% solids using a standard funnel, of between from about 7 to less than 20 seconds. The glaze base may further comprise a low molecular weight carbohydrate having less than 10 sugar units. Alternatively, the glaze base may consist essentially of the converted starch. Such a glaze base is further characterized by a DE of greater than about 20.

The invention also relates to a process for preparing the converted starch comprising hydrolyzing a base starch with a combination of alpha-amylase and another amylase enzyme. Aqueous solutions of converted starches prepared according to this process demonstrate excellent viscosity stability.

The present invention is also directed to a glaze for foods comprising the glaze bases of the present invention and the foods prepared therefrom.

DETAILED DESCRIPTION

All starches and flours (hereinafter "starch") may be suitable for use as the base starch from which the converted starch of the glaze bases of the present invention are prepared, and may be derived from any native source. A native starch as used herein, is one as it is found in nature. Also suitable are starches derived from a plant obtained by standard breeding techniques including crossbreeding, translocation, inversion, transformation or any other method of gene or chromosome engineering to include variations thereof. In addition, starches derived from a plant grown from artificial mutations and variations of the above generic composition which may be produced by known standard methods of mutation breeding are also suitable for use as the base starch herein.

Typical sources for the base starches are cereals, tubers, roots, legumes and fruits. The native source can be corn, pea, potato, sweet potato, banana, barley, wheat, rice, sago, amaranth, tapioca, arrowroot, canna, sorghum, and waxy or high amylose varieties thereof. As used herein, the term "waxy" is intended to include a starch or flour containing at least about 95% by weight amylopectin and the term "high amylose" is intended to include a starch or flour containing at least about 40% by weight amylose.

Chemically modified starches may also be used as the base starch. Such chemical modifications are intended to include, without limitation, crosslinked starches, acetylated and organically esterified starches, hydroxyethylated and hydroxypropylated starches, phosphorylated and inorganically esterified starches, cationic, anionic, nonionic, and zwitterionic starches, and succinate and substituted succinate derivatives of starch. Particularly useful are food-grade chemical modifications including acetylated, hydroxyalkylated, phosphorylated, succiniate and substituted succinate derivatives of starch. Procedures for modifying starches are well-known and described, for example in *Modified Starches: Properties and Uses,* Ed. Wurzburg, CRC Press, Inc., Florida (1986).

Conversion products derived from any of the aforementioned starches may also be used as the base starch, including fluidity or thin-boiling starches prepared by oxidation, enzyme conversion, acid hydrolysis, heat and or acid dextrinization. Thermally-treated and or sheared products may also be useful herein.

Physically modified starches may also be used as the base starch, including, without limitation, thermally inhibited or pregelatinized starches. Procedures for preparing thermally inhibited starches are disclosed, for example, in U.S. Pat. No. 6,221,420, and references disclosed therein, the disclosure of which is incorporated by reference. Exemplary processes for preparing pregelatinized granular starches are disclosed in U.S. Pat Nos. 4,280,851, 4,465,702, 5,037,929, and 5,149,799, the disclosures of which are incorporated by reference.

The present invention is directed to a method for glazing a food product comprising the steps of:
a) applying an aqueous solution containing from about 25% to about 65% by weight of a glaze base containing a converted starch to the food; and b) drying the food;

wherein the glaze base has a funnel viscosity, measured at 19% solids using a standard funnel, of between from about 7 to less than 20 seconds. particularly between about 7 to about 15 seconds and more particularly between about 7 to about 10 seconds.

Glaze bases of the present invention may further comprise a low molecular weight carbohydrate having less than 10 sugar units. Particularly useful carbohydrates include, without limit, mono- and di-saccharides, and corn syrup solids. Where the glaze comprises a mixture of components, such as a converted starch and a low molecular weight carbohydrate, the components are blended together according to methods well-know in the art to afford a glaze base of the appropriate funnel viscosity.

Where the glaze base consists essentially of the converted starch, the glaze base is further characterized by a DE of greater than 20, and particularly a DE between greater than 20 and 40.

The converted starch may be prepared from a base starch by methods well-known in the art including, without limitation, enzymatic hydrolysis, conventional acid conversion procedures, and oxidative degradation methods such as those described in U.S. Pat. Nos. 4,838,944 and 5,833,755, the disclosures of which are incorporated herein by reference.

A particularly suitable process for preparing the converted starch comprises hydrolyzing a base starch with alpha amylase in combination with another amylase enzyme. Other amylase enzymes that may be used in combination with alpha amylase to hydrolyze the starch include, without limitation, beta-amylase, phosphorylase, isoamylase, pullulanase, and glucoamylase. Particularly useful amylases are beta-amylase and glucoamylase. The hydrolysis may be conducted via a dispersion or slurry method. The use of alpha-amylase in combination with beta-amylase via both methods is described below.

According to the dispersion method, the base starch is steam cooked, i.e., "jet cooked", by which is meant that it is slurried and heated to temperatures of about 120 to 170° C., in order to completely gelatinize the starch. The steam cooking is generally carried out in a slurry at a solids level of about 10 to 45%, preferably 20 to 35%, a pH of 4 to 7, preferably 5.0 to 6.5, with a pressure greater than 60 psi in the cooking chamber.

The resultant fully gelatinized starch is then enzymatically hydrolyzed using a combination of alpha amylase with another amylase, including either beta-amylase or glucoamylase, using techniques known in the art and described, for example, in U.S. Pat. Nos. 3,525,672 to Wurzburg et al. and 4,977,252 to Chiu.

For example, after the jet-cooking process is completed, the temperature is lowered and beta-amylase is added at 0.4% level. The enzyme treatment is carried out at a starch concentration level of about 10 to about 45%, preferably about 20 to about 24%, depending upon the base starch being treated. The enzyme reaction is continued until the starch is sufficiently degraded to provide a viscosity of about 20 seconds to about 30 seconds according to the flow viscosity test described infra.

The beta-amylase is then deactivated by increasing the temperature to above 85° C. for at least 20 minutes. Then, the temperature of the reaction mixture is lowered to about 65° C. and alpha-amylase is added at about the 0.001% level and the starches is further converted to a viscosity of between about 7 to about 20 seconds, particularly between about 7 to about 25 seconds and more particularly between about 7 to about 10 seconds.

According to the slurry method, the pH of a slurry of the base starch is adjusted to about 6.2 and then alpha amylase is added at about the 0.005% level. The temperature of the slurry is then slowly increased to 90° C., until the starch is degraded to a viscosity of between about 50 seconds to about 60 seconds according to the flow viscosity test described infra. The enzyme is then de-activated by lowering the pH of the reaction to between about 2.9 to 3.0 with a hydrochloric acid solution for more than 15 minutes. The pH is then adjusted to 5.7 and the temperature of the solution lowered to about 57° C. Beta-amylase, for example, may then added at about the 0.4% level and the starch further converted until a viscosity has been attained of between about 7 to about 20 seconds, particularly between about 7 to about 25 seconds and more particularly between about 7 to about 10 seconds. The beta-amylase is then de-activated by heat (temperature greater than 85° C. for more than 20 minutes).

One of skill in the art understands that the same flow viscosities can be obtained by varying the levels of enzyme involved and adjusting the time of the reaction accordingly.

In addition to having a flow viscosity of between 7 and less than 20 seconds, glaze bases consisting essentially of the converted starch which is hydrolyzed as described by the aforementioned processes involving a combination of alpha-amylase and another amylase including beta-amylase or glucoamylase, are characterized by a dextrose equivalent (DE) of greater than 20, particularly between greater than 20 to about 40. Dextrose equivalent is defined as the reducing power of the hydrolyzate. Each starch molecule has one reducing end, therefore DE is inversely related to molecular weight. The DE of anhydrous D-glucose is defined as 100 and the DE of unhydrolyzed starch is virtually zero.

The glaze bases made by any of the above methods may be used in the glazes of the present invention directly in liquid form or may be recovered in a shelf-stable powder form by spray drying, drum drying or other drying techniques known in the art. The glazes comprising the glaze bases of the present invention are characterized by low viscosity and may be prepared at solids concentrations of up to 65%.

Also, aqueous solutions of glaze bases consisting essentially of the converted starch which is hydrolyzed as described by the aforementioned processes with a combination of alpha-amylase with either beta-amylase or glucoamylase demonstrate excellent viscosity stability. In particular, a 30% solids solution of the converted starch exhibits a Brookfield viscosity increase of less than 10% over five days time. At a solids content of 60%, these converted starch solutions demonstrate a viscosity increase of less than 5% over 5 days.

Upon application, the glaze bases of the present invention also demonstrate greater gloss values than other glazes known in the industry. For example, at identical weights of dried sheen, the gloss values of the converted starches of the present invention are at least 1.5 times greater, particularly about 2 times greater and more particularly about 3 times greater than the beta-amylase treated starches described in U.S. Pat. No. 5,599,569, incorporated herein by reference.

Additionally, when applied to foods, the glazes comprising the glaze bases of the present invention are also quick drying, providing a good seal upon drying so as to extend the shelf life or the bowl life, preserve the desired flavors and increase the crispness of the food product on which it is used.

In preparing desirable glazes for food application, glaze bases of the present invention may be used alone, or blended with other components typical of glazes.

Ordinarily, the application process involves dissolving the converted starch product of the present invention in water at a solids content of 25% or above, depending upon the particular food application involved. The lowest viscosity converted starches prepared according to the present invention may be applied in as high as a 65% solids solution.

The solution ("glaze") is then applied to the surfaces of foodstuffs such as cereal pieces, cookies, biscuits, etc., using conventional processes such as the spray method, sponge roller method, brush application method, or immersion method. The foodstuff is then dried according to conventional techniques including oven and air-dryng.

Foods on which the glazes of the present invention are useful include, without limitation, pastries; bread; rolls; buns; cookies; crackers; breadsticks; croissants; bagels; Danish; pie components including crusts, as well as their frozen, unbaked and par-baked products; snack products including pretzels, snack mixes, peanut crackers, cereal bars; and confectioneries.

The following methods and examples are presented to further illustrate and explain the present invention and should not be taken as limiting any any regard. All parts and percentages are given by weight and all temperatures in degrees Celsius (° C.) unless otherwise noted.

EXAMPLES

Measurement of Flow Viscosity (19% solids)

The starch dispersion is adjusted to 19% (w/w) measured by refractometer. The temperature of the dispersion is controlled at 22° C. A total of 100 ml of the starch dispersion is measured into a graduated cylinder. It is then poured into a calibrated funnel while using a finger to close the orifice. A small amount is allowed to flow into the graduate to remove any trapped air, and the balance is poured back into the funnel. The graduated cylinder is then inverted over the funnel so that the contents draw (flow) into the funnel while the sample is running. Using a timer, the time required for the 100 ml sample to flow through the apex of the funnel is recorded.

The glass portion of the funnel is a standard 58°, thick-wall, resistance glass funnel whose top diameter is about 9 to 10 cm with the inside diameter of the stem being about 0.381 cm. The glass stem of the funnel is cut to an approximate length of 2.86 cm from the apex, carefully firepolished, and refitted with a long stainless steel tip which is 5.08 cm long with an outside diameter of 0.9525 cm. The interior diameter of the steel tip is 0.5951 cm at the upper end where it is attached to the glass stem; it is 0.4445 cm at the outflow end, with the restriction in the width occurring at about 2.54 cm from the ends. The steel tip is attached to the glass funnel by means of a Teflon tube. The funnel is calibrated so as to allow 100 ml of water to go through in 6 seconds using the above procedure.

Example 1

This example illustrates the preparation of the converted starches of the present invention via the dispersion method.

Slurry 2.0 kg of waxy corn starch (available from National Starch & Chemical Company) in 5.0 liters of top water in a plastic bucket. Adjust pH to 5.6–5.7 with 10% hydrochloric acid solution and jet-cook starch at 310 F (154° C.) and full steam to produce a starch dispersion of about 20–24% solids. After the jet cooking process is completed, cool down the starch to 57° C. in a reaction tank. Add 8.0 grams of beta-amylase solution (Spezyme BBA®1500, Genencor International) to promote starch degradation. Once the desired viscosity specification (20–25 seconds as measured at 19% solids and room temperature with 100 ml using standard funnel) is reached, stop the conversion by rapidly heating the dispersion to 85° C. and hold for about 20 minutes. Continue in the same conversion tank; lower the temperature of starch cook to 65° C. Add 0.02 grams of alpha-amylase (Ban 240L, Novo Nordisk) to further digest the starch. When the desired viscosity specification (7.3–7.5 seconds as measured at 19% solids and room temperature with 100 ml using standard funnel) is reached, stop the conversion. To denature the enzyme, lower the pH to 2.8 with 10% hydrochloric acid and hold for about 20 minutes. Finally, readjust the pH to 5.5–5.8 and spray-dry the dispersion to obtain a powdered product.

This procedure has also been conducted using as the base starch a waxy corn starch which has been acid-degraded via conventional procedures to a water fluidity of 50 as measured by test. These procedures and water fluidity tests, as used throughout this application are described in the Handbook of Water-Soluble Gums & Resins, M. W. Rutenberg, *Starch and Its Modifications,* Chapter 22, pg 32–33, edited by R. L. Davidson, McGraw-Hill (1980).

Example 2

This example illustrates the preparation of the converted starches of the present invention via the slurry method.

Slurry 2.0 kg of waxy corn starch in 3.5 liters of top water in a conversion vessel. Adjust pH to 6.2–6.4 and add 0.1 grams of alpha-amylase (Ban 240L, Novo Nordisk) to the starch slurry. Implement a controlled heating; slowly increase the temperature to 90° C. to disperse the starch in the presence of enzyme. Once the desired viscosity specification (50–60 seconds as measured at 19% solids and room temperature with 100 ml using standard funnel) is reached, deactivate the enzyme. Lower the pH to 2.8–3.0 with 10% hydrochloric acid solution and hold for about 15 minutes. Continue in the same reaction tank; readjust the pH to 5.7 with 3% NaOH solution and lower the temperature to 57° C. Add 8.0 grams of beta-amylase solution (Spezyme BBA®1500, Genencor International) to degrade the starch. When the desired viscosity specification (7.3–7.5 seconds as measured at 19% solids and room temperature with 100 ml using standard funnel) is reached, denature the enzyme by a rapid heating to 85° C. for about 20 minutes. Next, the highly degraded starch is jet-cooked at 300° F. (149° C.) and full steam. Finally, spray-dry the dispersion to obtain a powder.

Converted starches have been prepared via this method using both a waxy potato starch and a waxy corn starch treated with 7% propylene oxide based on the weight of the starch (both available from National Starch & Chemical Company) as base starches.

Example 3

This example illustrates the preparation and properties of the glaze bases according to the present invention.

A waxy maize starch converted to a water fluidity of 80 WF by conventional acid conversion procedures was blended with corn syrup solids to produce a glaze base having flow viscosity levels of between 7.0 to 10 as measured by the test described above. These properties of these glaze bases were compared to a base consisting essentially of a waxy maize starch converted via the procedure of Example 1.

TABLE 1

Physical Properties of Glaze Bases Containing Acid Converted Starch ("Starch") and Corn Syrup Solids ("CSS") and Converted Starch prepared via Example 1.

| Starch/CSS (wt % ratio) | Viscosity (CML123E) | % Solids | Gloss Values |
|---|---|---|---|
| 25/75 | 7.7 sec | 60% | 84.2 |
| 15/85 | 7.3 sec | 60% | 82.4 |
| 100% starch via Example 1 | 7.8 sec | 60% | 89.5 |

As reported in the Table above, glaze bases prepared according to the present invention can be used at a suitably high solids content to prepare glazes have a good glaze.

Example 4

This example illustrates the improved gloss that the converted starches prepared by enzymatic hydrolysis as described by the present invention demonstrate over other converted starches.

Solutions of the converted starch prepared according to Example 1 were made at 30%, 50% and 60% solids content. The gloss of these solutions were compared to another enzymatically converted starch known in the industry (the "Control", waxy corn starch, jet-cooked and treated with beta-amylase according to the procedures described in U.S. Pat. No. 5,599,569). Because of the undesirable viscosity of these starches, the Control could only be prepared at a maximum 30% solids content.

For each measurement, 10 crackers were selected and their initial weight recorded. Each starch solution was applied to each of the crackers using either the "brushing on" or "spraying on" techniques. Immediately after the sheen application, the selected batch of crackers were placed into the 300° F. oven and dried for 5 minutes. After the drying step, the weight of the sample was recorded.

TABLE 2

Gloss Values of Converted Starches

| Starch | Technique | Solids | Weight of the sheen (after oven drying) | Quality/appearance of sheen |
|---|---|---|---|---|
| Control | Brush (thin) | 30% | 0.97 g | Good, light gloss |
|  | Brush on (thick) | 30% | 2.86 g | Dull gloss, soft cookie |
|  | Spray on (thin) | 30% | 0.2 g | No sheen, no gloss |
|  | Spray on (thick) | 30% | 0.7 g | Light gloss, ok sheen |
| Example 1 | Brush on (thin) | 60% | 0.61 g | Great sheen, high gloss |
|  | Brush on (thick) | 60% | 1.52 g | Great sheen, high gloss |
|  | Spray on (thin) | 50% | 0.22 g | Some sheen, light gloss |
|  | Spray on (thick) | 50% | 0.57 g | Good sheen, light gloss |
|  | Brush on (thick) | 30% | 0.72 g | No sheen, no gloss |

The data recorded in Table 2 demonstrate that the enzymatically hydrolyzed starches described in the present invention enabled the development of a glaze for foods having high gloss using relatively little material irrespective of the method of application as compared to other enzymatically converted starches.

Example 5

This example illustrates the excellent viscosity stability of the starches of the present invention which are prepared by enzymatic hydrolysis as described herein.

Starches of the present invention were prepared according to Examples 1 and 2 and solutions were made of each starch at 30% and 60% solids. The viscosities of these starch solutions were measured at 5 hours, 24 hours, 72 hours and 5 days after preparation.

An RVT model Brookfield Viscometer (available from Brookfield Engineering Laboratories, Inc.) was used for viscosity measurements. The Brookfield was set at 10 rpm using spindle 5. All viscosities are reported in centipoise ("cps") and were measured at 72° F.

TABLE 3

Brookfield Viscosity Measurements of Converted Starches

| Glaze base Preparation | Solution % solids | Viscosity (cps) | | | |
|---|---|---|---|---|---|
| | | 5 hours | 24 hours | 72 hours | 5 days |
| Example 1 | 60% | 1000 | 1000 | 1000 | 1000 |
|  | 30% | 90 | 100 | 100 | 100 |
| Example 2 | 60% | 3100 | 3200 | 3200 | 3200 |
|  | 30% | 110 | 120 | 120 | 120 |

The data reported in Table 3 demonstrates that the converted starches prepared via the enzyme hydrolysis described in the present invention demonstrate a viscosity increase of less than 10% at a 30% solids content and less than 5% at a 60% solids content level over five days time.

Example 6

This example demonstrates that the converted starches of the present invention which are prepared by enzymatic hydrolysis described herein demonstrate superior gloss at less weight ("sheen weight") than other enzymatically converted starches known in the industry.

Starches of the present invention were prepared according to the procedures of Examples 1 and 2 and solutions were made of each starch at 30% and 50% solids. An enzymatically converted starch was also prepared according to the description in Example 3 ("Control", prepared according to U.S. Pat. No. 5,599,569) and a 30% solution made.

Paper was weighed and a film of 30 and 50% starch solutions were "drawn" on the paper. The paper and film were weighed, then placed in a 50° C. draft oven for one minute. The paper and film were weighed again and the anhydrous weight of the sheen recorded according to the following formula:

Actual sheen weight (grams)=weight of paper and sheen after drying (gram)−weight of paper (grams)+0.4 (grams).

The 0.4 grams was added to correct for the moisture of the paper that was lost during drying.

A Glossmeter (Hunterlab modular model D-48-7, commercially available from Hunter Associates Laboratory, Inc., Reston, Va.) was calibrated with a black glass standard. The value of the standard (85% ASTM gloss values) was determined by its index of refraction.

The sheen weight, solids content and corresponding gloss units of the prepared glazes are presented in Table 4.

TABLE 4

Relative Gloss Values and Sheen Weight of Converted Starches

| Glaze base Preparation | Gloss unit average | Solids % | Sheen weight |
| --- | --- | --- | --- |
| Example 1 | 79.34 | 50% | 0.64 g |
| Example 2 | 75.28 | 50% | 0.7 g |
| Control | 25.62 | 30% | 0.63 g |

The data reported in Table 4 illustrates that the glaze bases consisting essentially of the converted starches prepared via the enzymatic hydrolysis procedures described herein demonstrate a superior gloss at similar material weights as compared to other enzymatically converted starches known in the industry.

We claim:

1. A method for glazing foods comprising the steps of:
   applying to the food a solution containing from about 25% to about 65% by weight of a glaze base containing a converted starch; and
   drying the food;
   wherein the glaze base has a funnel viscosity, measured at 19% solids using a standard funnel, of between from about 7 to less than 20 seconds, and
   wherein the converted starch is prepared by enzymatically hydrolyzing a base starch with at least two enzymes.

2. The method of claim 1 wherein the glaze base has a funnel viscosity of between about 7 to about 15 seconds.

3. The method of claim 2 wherein the glaze base has a funnel viscosity of between about 7 to about 10 seconds.

4. The method of claim 1 wherein the glaze base further comprises a low molecular weight carbohydrate having less than 10 sugar units.

5. The method of claim 1 wherein the glaze base has a DE greater than about 20.

6. The method of claim 1 wherein the converted starch is a waxy starch.

7. The method of claim 1 wherein the converted starch is a chemically modified starch selected from the group consisting of acetylated, hydroxyalkylated, phosphorylated, succinate and substituted succinate derivatives.

8. The method of claim 1 wherein the converted starch is prepared by enzymatically hydrolyzing a base starch with a combination of alpha-amylase and another enzyme.

9. The method of claim 8 wherein the another enzyme is selected from the group consisting of beta-amylase and glucoamylase.

10. The method of claim 1 wherein the glaze base consists essentially of the converted starch and a 30% solids solution of the converted starch demonstrates a Brookfield viscosity increase of less than 10% over five days time.

11. The method of claim 1 wherein the base starch is hydrolyzed via a dispersion method with beta-amylase to give a partially degraded starch having a flow viscosity of between from about 20 seconds to about 30 seconds; and the partially degraded starch is then treated with alpha-amylase.

12. The method of claim 11 wherein the partially degraded starch has a flow viscosity of between from about 20 seconds to about 25 seconds.

13. The method of claim 1 wherein the base starch is hydrolyzed via a slurry method with alpha-amylase to give a partially degraded starch having a flow viscosity of between about 50 seconds to about 80 seconds, and the partially degraded starch is then treated with beta-amylase.

14. The method of claim 13 wherein the partially degraded starch has a flow viscosity of between about 50 seconds to about 60 seconds.

15. The method of claim 1 wherein the glaze base contains from about 10 to about 30% by weight of the converted starch.

16. A process for preparing a converted starch comprising enzymatically hydrolyzing a base starch with at least two enzymes in an amount for a for a sufficient time to achieve a funnel viscosity, measured at 19% solids using a standard funnel, of between from about 7 to less than 20 seconds; and a DE of greater than about 20.

17. The process of claim 16 wherein the base starch is hydrolyzed to a funnel viscosity of between from about 7 seconds to about 15 seconds and a DE of between greater than about 20 to about 40.

18. The process of claim 17 wherein the base starch is hydrolyzed to a funnel viscosity of between from about 7.0 seconds to about 10.0 seconds.

19. A glaze base prepared with the converted starch prepared according to the process of claim 16.

20. A glaze for foods comprising the glaze base of claim 19.

21. The glaze according to claim 20 wherein the food is selected from the group consisting of pastries, bread, rolls, buns, cookies, crackers, breadsticks, croissants, bagels, Danish, pie components, snack products and confectioneries.

22. A converted starch prepared according to the process of claim 16 wherein a 30% solids solution of the converted starch demonstrates a Brookfield viscosity increase of less than 10% over five days time.

\* \* \* \* \*